(12) United States Patent
Keating et al.

(10) Patent No.: US 11,006,952 B2
(45) Date of Patent: May 18, 2021

(54) FIXATION DEVICE DELIVERY SYSTEM

(71) Applicant: SHARP FLUIDICS, LLC, Hayward, CA (US)

(72) Inventors: Ronan Keating, Dublin (IE); Diarmuid Conroy, Dublin (IE); Gerard Rabbitte, Dublin (IE)

(73) Assignee: SHARP FLUIDICS, LLC, Hayward, CA (US)

( * ) Notice: Subject to any disclaimer, the term of this patent is extended or adjusted under 35 U.S.C. 154(b) by 228 days.

(21) Appl. No.: 16/070,255

(22) PCT Filed: Jan. 13, 2017

(86) PCT No.: PCT/EP2017/050703
§ 371 (c)(1),
(2) Date: Jul. 13, 2018

(87) PCT Pub. No.: WO2017/121870
PCT Pub. Date: Jul. 20, 2017

(65) Prior Publication Data
US 2019/0021727 A1    Jan. 24, 2019

Related U.S. Application Data

(60) Provisional application No. 62/278,139, filed on Jan. 13, 2016.

(51) Int. Cl.
*A61B 17/068* (2006.01)
*A61B 17/064* (2006.01)
(Continued)

(52) U.S. Cl.
CPC ............ *A61B 17/068* (2013.01); *A61B 17/06* (2013.01); *A61B 17/064* (2013.01); *A61B 17/32* (2013.01);
(Continued)

(58) Field of Classification Search
CPC ..... A61B 17/068; A61B 17/06; A61B 17/064; A61B 17/32; A61B 17/105;
(Continued)

(56) References Cited

U.S. PATENT DOCUMENTS 8,474,679 B2    7/2013    Felix
2010/0001038 A1*    1/2010    Levin .................. A61B 17/068
227/179.1

(Continued)

FOREIGN PATENT DOCUMENTS

EP    2870929 A1    5/2015
JP    2007-500583 A    1/2007
(Continued)

OTHER PUBLICATIONS

International Search Report for PCT/EP2017/050703 dated May 11, 2017; 7 pages.

*Primary Examiner* — Tuan V Nguyen
(74) *Attorney, Agent, or Firm* — FisherBroyles LLP; John Shimmick

(57) ABSTRACT

A fixation device delivery system is described. The system includes a driver and a cooperating fixation element featuring a barb which becomes active upon deployment in the inner abdominal wall.

35 Claims, 14 Drawing Sheets

(51) Int. Cl.
*A61B 17/32* (2006.01)
*A61F 2/00* (2006.01)
*A61B 17/06* (2006.01)
*A61B 17/00* (2006.01)

(52) U.S. Cl.
CPC .. *A61F 2/0063* (2013.01); *A61B 2017/00004* (2013.01); *A61B 2017/0648* (2013.01); *A61B 2017/320044* (2013.01); *A61F 2002/0072* (2013.01); *A61F 2210/0004* (2013.01); *A61F 2220/0016* (2013.01)

(58) Field of Classification Search
CPC ..... A61B 2017/0647; A61B 2017/0648; A61F 2/0063
See application file for complete search history.

(56) References Cited

U.S. PATENT DOCUMENTS

| | | | | |
|---|---|---|---|---|
| 2010/0312257 | A1* | 12/2010 | Aranyi | A61B 17/064 606/139 |
| 2011/0022065 | A1* | 1/2011 | Shipp | A61B 17/0644 606/151 |
| 2011/0071578 | A1* | 3/2011 | Colesanti | A61B 17/064 606/305 |

FOREIGN PATENT DOCUMENTS

| | | | |
|---|---|---|---|
| WO | 2007/086832 | A2 | 8/2007 |
| WO | 2007/098512 | A1 | 9/2007 |
| WO | 2010/123740 | A1 | 10/2010 |

* cited by examiner

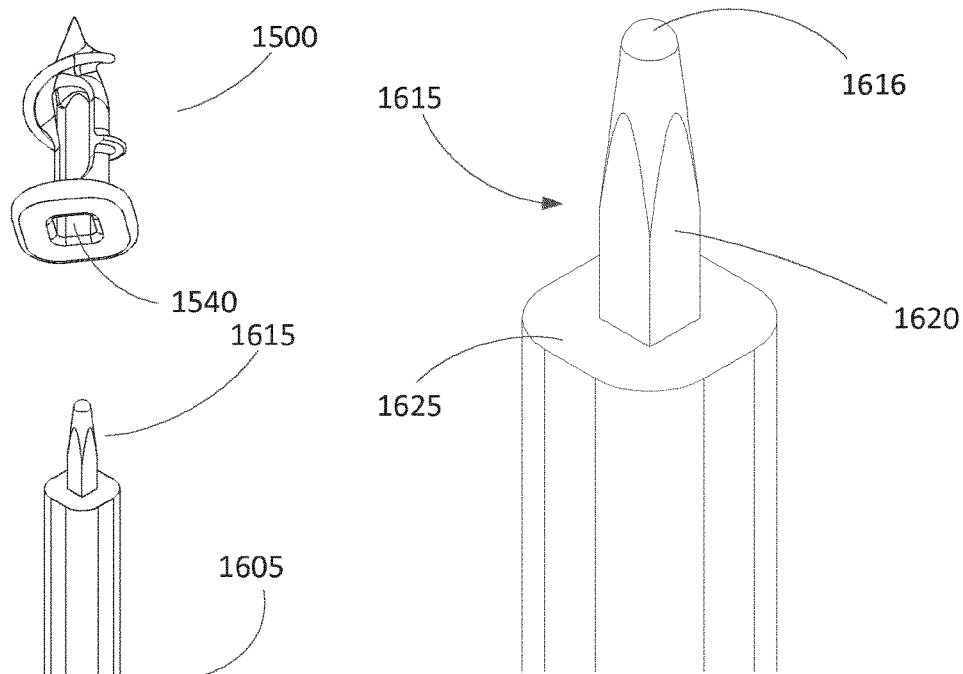
Figure 8
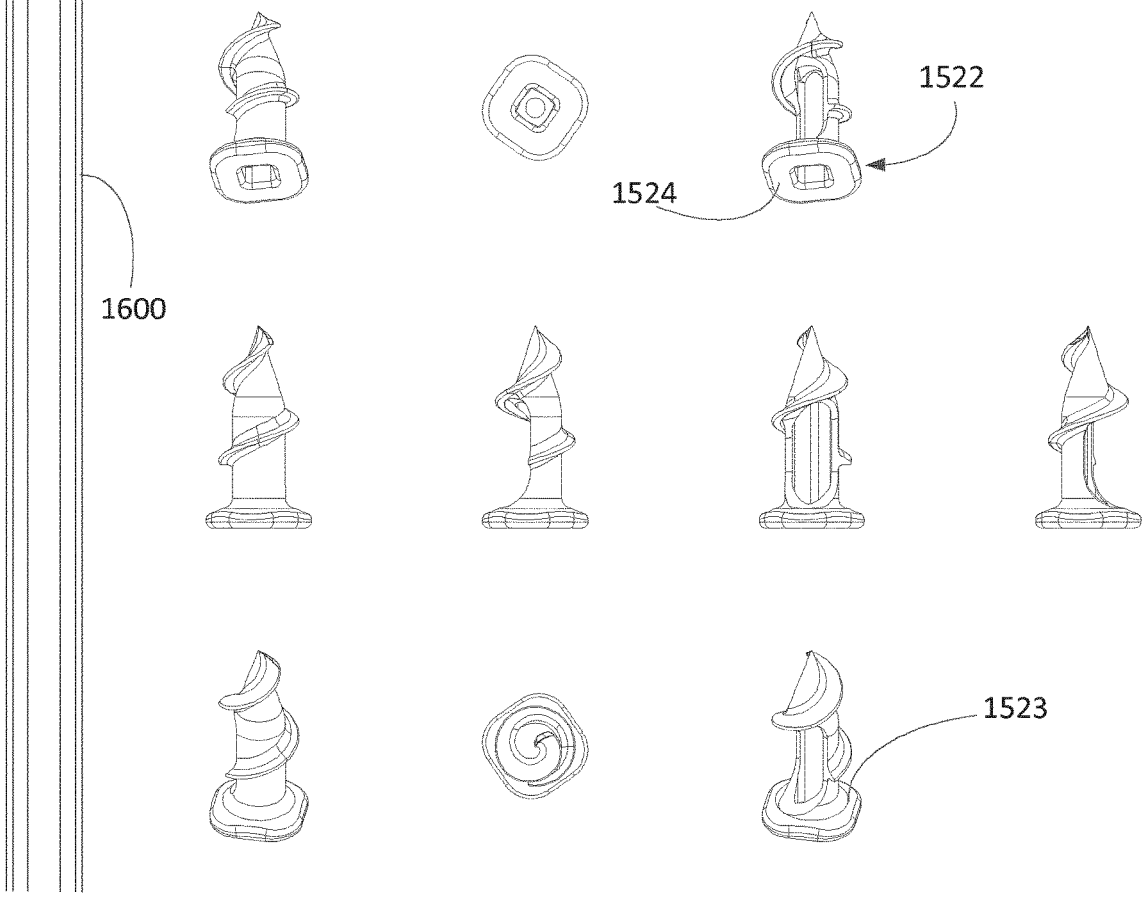
Figure 7
Figure 9

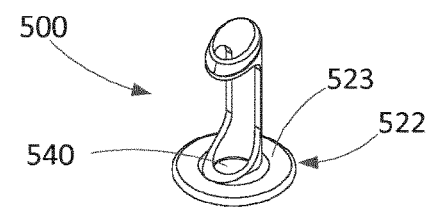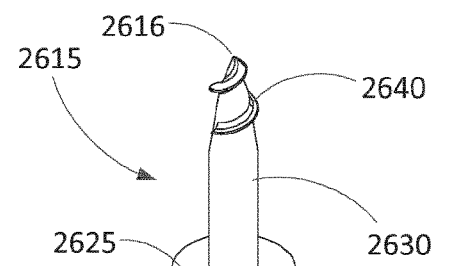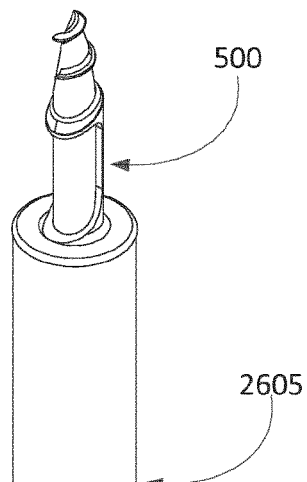
Figure 12A          Figure 12B

FIXATION DEVICE DELIVERY SYSTEM

CROSS-REFERENCE TO RELATED APPLICATION

The present application is a national phase entry under 35 U.S.C. § 371 of International Application No. PCT/EP2017/050703, filed Jan. 13, 2017, entitled "FIXATION DEVICE DELIVERY SYSTEM," which designates the United States of America, and claims priority to U.S. Provisional Patent Application No. 62/278,139, filed Jan. 13, 2016, the entire disclosures of each are hereby incorporated by reference in their entireties and for all purposes.

FIELD OF THE INVENTION

The present invention relates to a fixation device delivery system.

BACKGROUND

Mesh placement is a common treatment in hernia repair and is increasingly completed laparoscopically. The procedure involves the surgeon first removing tissue from the defect in the abdominal wall to expose the opening. A repair mesh is then sized and inserted into the abdominal space. The mesh is then unfurled and positioned over the defect using graspers. Once the mesh is in position it is typically tacked in place using multiple tacks with a tacking device. Many known tacker devices are prone to jamming and some devices rely on the application of counter pressure on the external surface of the abdomen. A significant portion of the cost associated with tack delivery systems can be the absorbable material used to form the tack, these devices are not typically supplied with a flexible number of tacks which often results in too many tacks being deployed or a fraction of the supplied tacks being deployed. There are therefore a number of problems with current methods of mesh tacking that need to be addressed.

SUMMARY

Accordingly, there is provided a system and method as detailed in the independent claims. Advantageous embodiments are provided in the dependent claims.

A device, system and method per the present teaching may advantageously be used with tacks that are based on a two part construction, each of the two parts being coupled to one another using an interconnecting member. On deployment one of the parts is placed in the abdominal wall and becomes active as a barb, and the second part forms an abutment against the inner surface of the mesh so as to secure the mesh to the abdominal wall. This method of affixation may produce a lower tension fixation relative to helical designs and require less tacks as the tacks are more secure, and hence is advantageous over prior art implementations. Other types of tacks that may be employed are provided in a one part configuration which is seated on the delivery device and exposed during transportation from the abdominal wall to the delivery location where it is then embedded into tissue.

BRIEF DESCRIPTION OF THE DRAWINGS

The present invention will now be described with reference to the accompanying drawings in which:

FIGS. 7 and 8 show further embodiments of a fixation device delivery system or tack delivery instrument in isometric view.

FIG. 9 shows various views of the tack used in conjunction with the delivery instrument of FIGS. 7 and 8.

FIGS. 12A and 12B show a tack in conjunction with a delivery instrument in accordance with the present teaching.

DETAILED DESCRIPTION OF THE DRAWINGS

The teaching of the present invention will now be described with reference to exemplary embodiments thereof which are provided to assist with an understanding of the present teaching and are not to be construed as limiting in any way. It will be appreciated that modifications can be made to the exemplary arrangements which follow without departing from the spirit or scope which is only to be limited insofar as is deemed necessary in the light of the appended claims.

Within the context of the present teaching a fixation device delivery system advantageously allows for the delivery of a tack within an abdominal cavity of the patient. Within the context of the present teaching the terms "anchor", "fixation element", and "tack" will be used interchangeably. Where a plurality of fixation elements are used for fixation purposes, for example the fixation of a mesh within the abdominal cavity, they will typically be referred to as tacks. The terms "fixation device delivery system" and "tacking device" will also be used interchangeably. The term "delivery instrument" and "delivery driver" may also be considered as referring to the same or similar components.

It will be appreciated that the following discussion regarding the specifics of the abdominal cavity and abdominal wall should not be construed as limiting in that a system provided in accordance with the present teaching may be used with other types of tissue including but not limited to organs, bones or the like. The use of any tack delivery system per the present teaching can be used for one or more of tacking laparoscopic surgical equipment, assisting in the moving of internal organs to allow a surgeon access to a surgical site, The adoption of such techniques will advantageously require the use of bioabsorbable tacks, as the tacks will remain within the abdominal cavity during the healing process prior to their ultimate disintegration.

The tack may then be delivered to the surgical site through co-operation of the tack with a delivery tool. The delivery tool engages with the tack and is then used to deliver the tack through to the abdominal cavity. Such tack or tacks are advantageously used as fixation devices.

Figure 1C:
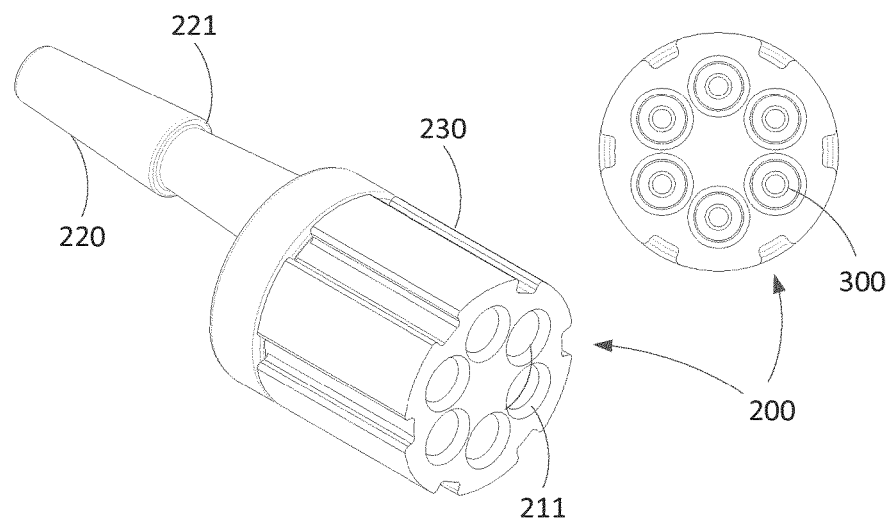
FIG. 1C shows more detailed view of the cartridge from the system of FIG. 1A in isometric views.

FIG. 1 illustrates driver device 100 which comprises a proximal handle 110 and a shaft 120. The handle comprises a surface 113 which will abut with the palm of a user's hand in use and surfaces 114 against which the fingers will engage. The shaft 120 has at its distal end a stepdown portion 115. This stepdown portion in turn at its distal end has a tip 125. The portion of the stepdown between the distal end of the shaft 120 and the proximal end of the tip 125 serves to act as a tack receiving portion. The stepdown portion could be manufactured from the same stock as the shaft and be machined, or could be an insertable part, held in place by a grub screw, or dowel type pin. It could be fabricated as a non-deformable core wire which could be finished with a sharp trocar style tip, or be a truncated trocar tip as illustrated here. The truncated trocar tip features tissue dissecting edges 126, which when rotated function to part tissue. The shaft could be bonded into the handle with adhesive, be over moulded by the handle, or be retained by a grub screw. In an iteration where the shaft is retained by a grub screw and the shaft and handle are manufactured from stainless steel or other autoclavable materials this driver portion of the device could be reusable.

An alternative construction, not shown, would be to have an auger style or helical tip on the non-deformable core wire. Such a construction would require the user to rotate the driver device 100 to engage the tip through the abdominal wall/mesh. Alternately the handle of the device could be supplied separately as a disposable element and feature a power pack so that the handle could drive the shaft to rotate it automatically. Alternatively the handle could be pneumatically powered.

In another iteration of the device, not shown, the shaft could be pivotable which would be advantageous in terms of enabling articulated delivery of tacks. In such a construct the core wire may be provided as a deformable core wire with a helical tip in order to allow transmission of rotation from the handle. For a tip design where rotation was not required to insert the tip, then the core wire could be non-deformable within the portion distal to the pivot point.

Alternatively the device could be articulating and be steerable via control wires. In such an embodiment the tack could be provided with cut outs to allow the control wires pass through the tack.

Figure 1B:
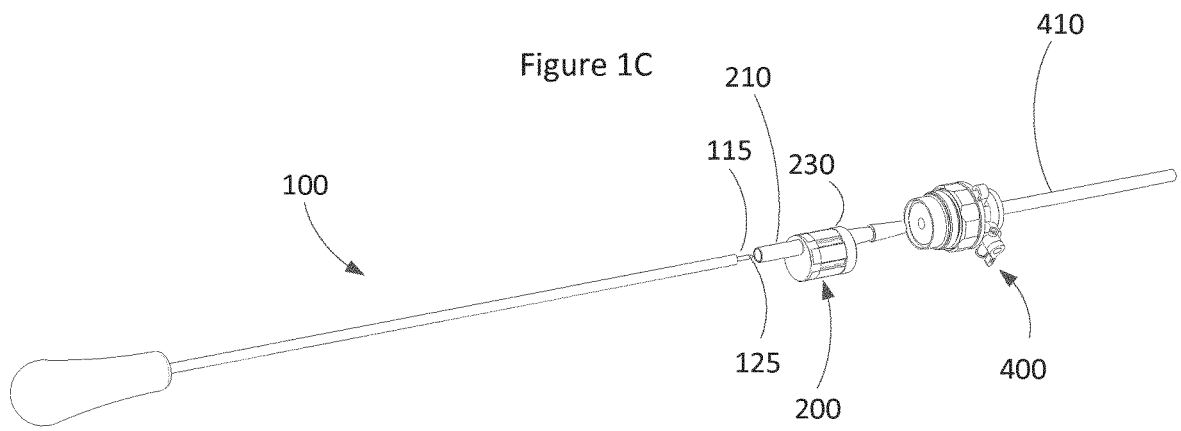
FIG. 1B shows more detailed view of the system of FIG. 1A in isometric and end elevation.
Figure 1A:
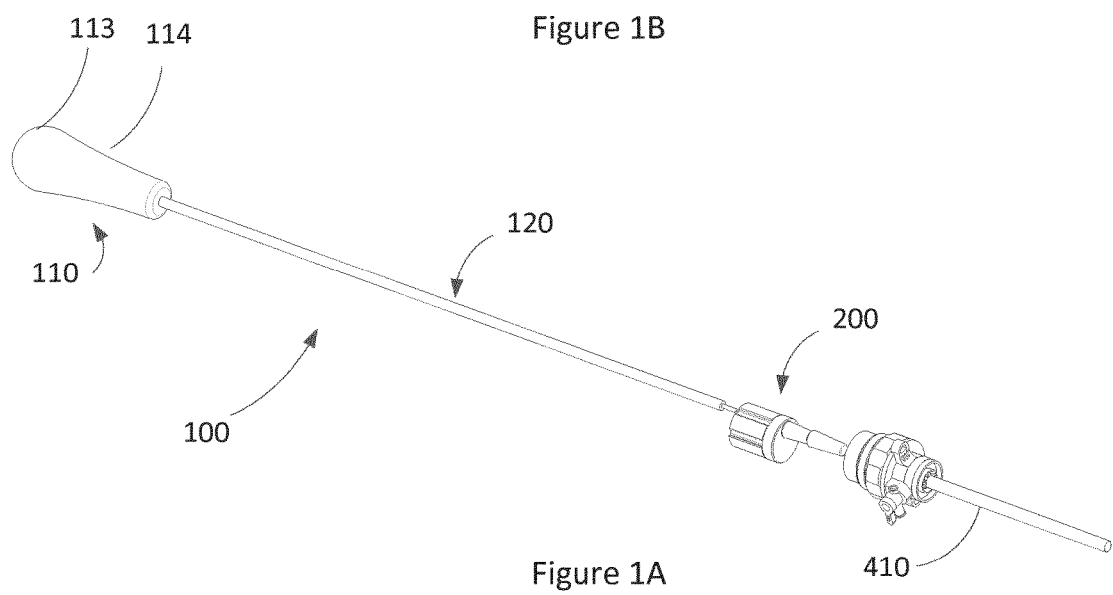
FIG. 1A show an example of a fixation device delivery system provided in accordance with the present teaching in isometric view.

Turning now to FIG. 1B, the driver device 100 in this aspect cooperatively interacts with a cartridge 200 which houses multiple tacks 300. The cartridge features a proximal lead in portion 210 in and a distal lead in portion 220 in the embodiment of FIG. 1B, and no proximal lead in portion in the embodiment of FIG. 1A. The advantage of the proximal lead in portion is that the driver device need not be retracted completely from the cartridge before loading the next anchor, which allows the user to maintain trocar position. A further modification could be made to the cartridge where a ball plunger in the cartridge interacts with a step on the shaft additional and proximal to the stepdown portion 115. This would function to prevent the driver from exiting the cartridge when it is pulled proximal and act as a cue to the user to begin advancing the driver again. The tip of the driver device 100 can be received in a proximal opening 211 of the cartridge. The proximal opening adjoins a lumen which runs through the cartridge and exits at the distal end of the distal lead in portion 220. This lumen is interrupted in the main body section 230 of the cartridge, where one of the pre-loaded tacks 300 is placed. Upon movement of the device through the cartridge a tack is picked up by the stepdown portion 115, and moved through the cartridge to exit at the distal end.

The distal lead in portion interacts with a trocar 400, such that the distal lead in portion is received in the lumen of the trocar 405. The distal lead in portion may feature a barb type feature 221, such that the cartridge is retained within the trocar due to an interaction of the trocar seal (not shown) with the barb 221. In addition the lead in portion 220 is sized to terminate in the shaft portion of the trocar 410.

The main body section 230 of the cartridge 200 is shown loaded with 6 tacks in this iteration, although it will be appreciated that the actual number used may well vary in application. Rotation of the main body section will move the next tack into the delivery lumen. For this to be achieved the user will first retract the driver device 100 to a point where the tip is proximal to the main body section. The main body section is then rotated to the next position. The main body section max feature a ball plunger and be indexed such that a click indicates when the next tack is aligned with the delivery lumen. An additional feature could be that the main body section 230 only rotates clockwise for example and that a simple ratchet mechanism prevents it from being rotated counter clockwise. This would ensure that each time the main body section is rotated, a tack is presented. In the cartridge a blind channel could be provided to indicate that no further tacks can be loaded, such that the tip 125 of the driver device 100 cannot advance further than the main body section. This may be especially useful where larger numbers of tacks are preloaded. Alternately, the cartridge could be sprung so that after each tack is deployed the cartridge rotates.

Figure 2C:
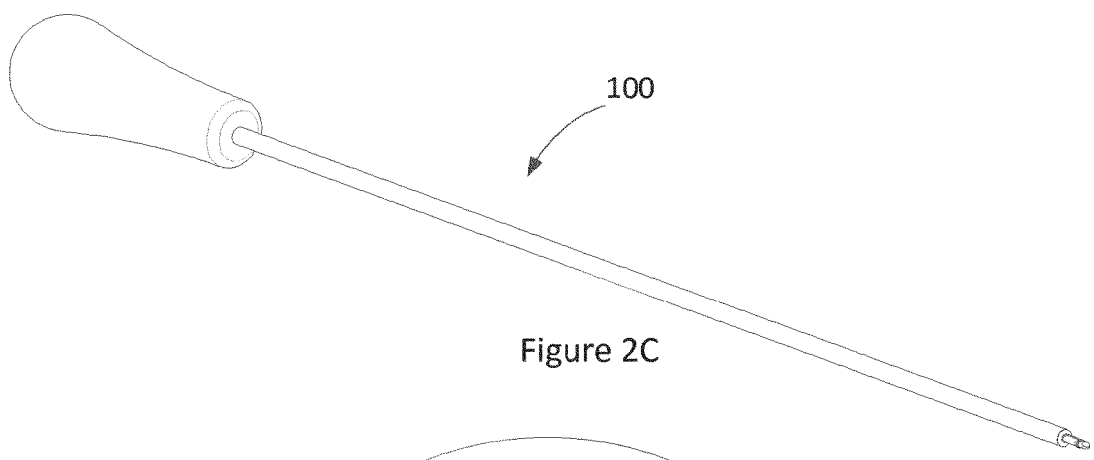
FIG. 2C show an example of the driver device of FIG. 1 with a loaded tack.

To use the devices of FIG. 1 the user:
a. Passes the cartridge into a trocar or port;
b. The user then passes the driver device 100 through the cartridge, picking up a tack in the process of doing so and advances the tip of the device to the desired location to place the tack;
c. The user deploys the tack at the desired location by applying pressure and rotating the device;
d. Following successful deployment of the tack, the driver device is retracted proximal to the main body section of the cartridge so that the next tack can be picked up on the next advancement of the device;
e. The cartridge is rotated to align the next anchor; Steps b to d are repeated to deploy the next tack. This process is repeated until the user is satisfied with that sufficient affixation has been achieved, or the device is emptied of tacks;

f. The device is removed from the trocar or port;

An embodiment of a tack is illustrated in FIG. 2, which shows a tack 300 which may be used in conjunction with the device of FIG. 1. The tack could be moulded from a bio-absorbable material. The material in a preferred embodiment is poly(lactic-co-glycolic acid), PLGA, but could be made in any ratios of the following materials PGA, PLLA, PDLGA, PLDLA or other absorbable or non-absorbable materials depending on the application.

1. The tack 300 features a distal tacking portion 320, and a proximal abutment portion 310, joined by an interconnecting member 330. The proximal portion 310 has an opening 305 through which the distal tip 125 of the driver device 100 initially passes. The tip 125, is similarly received through an opening 325 in the distal tacking portion. When the tack is deployed the tack is delivered until the surface 311 abuts with the abdominal wall and mesh. Upon removal of the tack receiving portion of the device 100 and in the absence of 115, a recessed portion 350 with 50% or more of the lumen is exposed. By having 50% or more of the tack lumen exposed along a longitudinal axis of the tack body, the tack when embedded into the tissue facilitates or promote tissue ingrowth after delivery. Tissue can invaginate into this recess, such that the rearward facing edge 321 now acts as a barb, catches on the tissue and prevents removal of the tack. In addition the exposed lumen promote tissue ingrowth after post procedure.

Figure 3C:
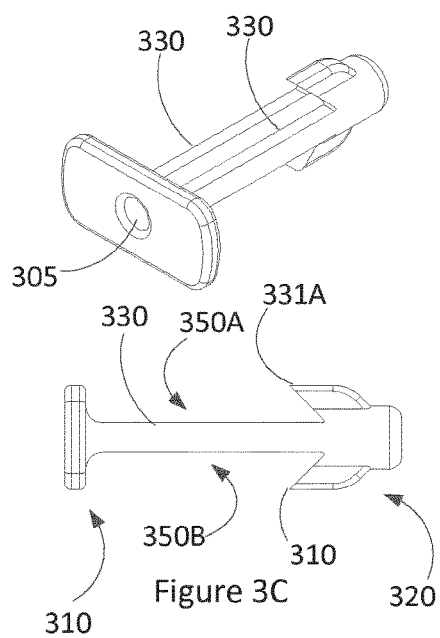
FIGS. 3A to 3D show alternate tack configurations that may be employed within the context of the present teaching.
Figure 3D:
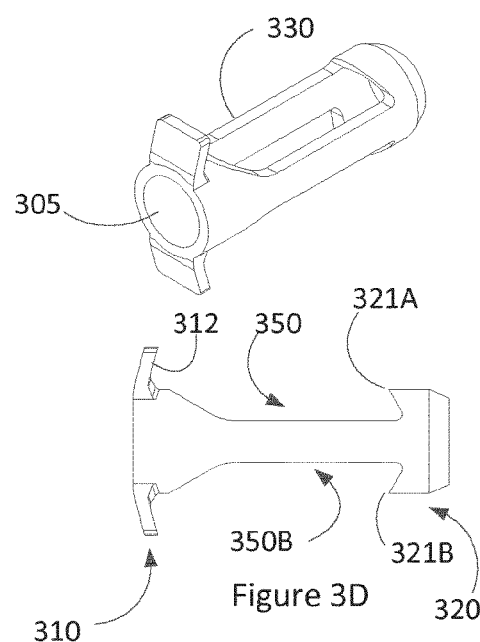
Figure 3A:
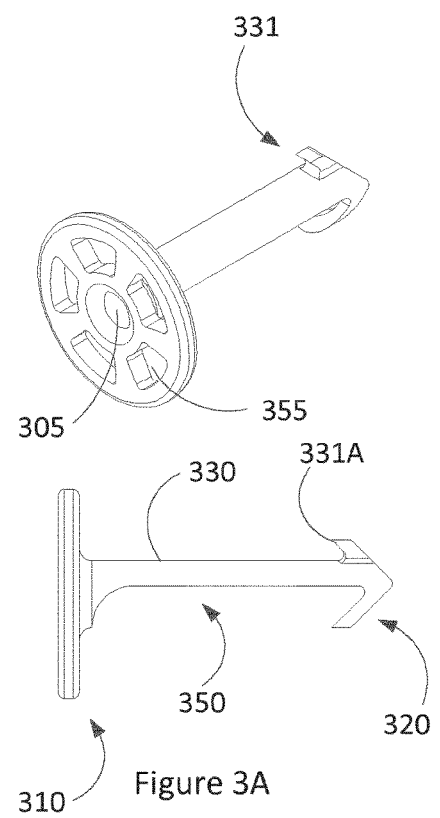
Figure 3B:
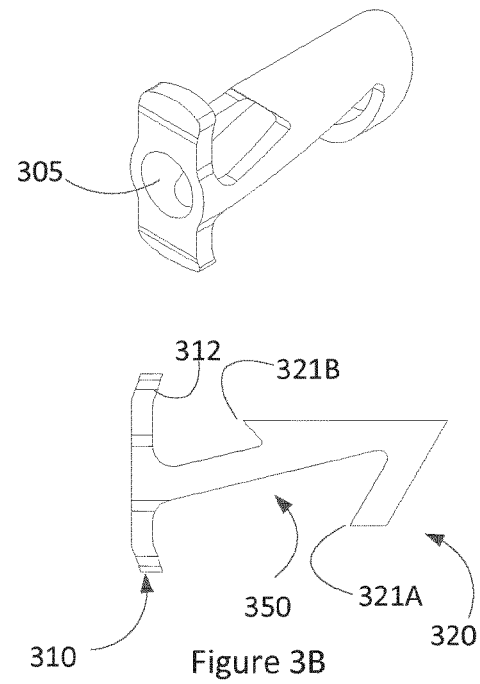

Alternative configurations of the tack could be provided as per FIG. 3B, with additional secondary barbs 321 to facilitate additional fixation of the tack. These secondary barbs function like the primary in that the only become active upon removal of the stepdown portion. Alternatively a further embodiment could feature barbs 331 on the outer surface of the tack, which unlike the primary barb, would be active throughout delivery, and serve to function as a means of deploying the anchor, as per the illustrations in FIG. 3A and FIG. 3C.

FIG. 3A depicts a tack featuring a number of windows 355, which serve to reduce the volume of implant while maximising the area of the tissue/mesh proximal contacting portion 310 of the tack. FIG. 3B and FIG. 3D illustrate the proximal contacting portion surface 312 angled towards the distal tip portion. This arrangement ensures better contact of the anchor with the mesh.

Figure 2B:
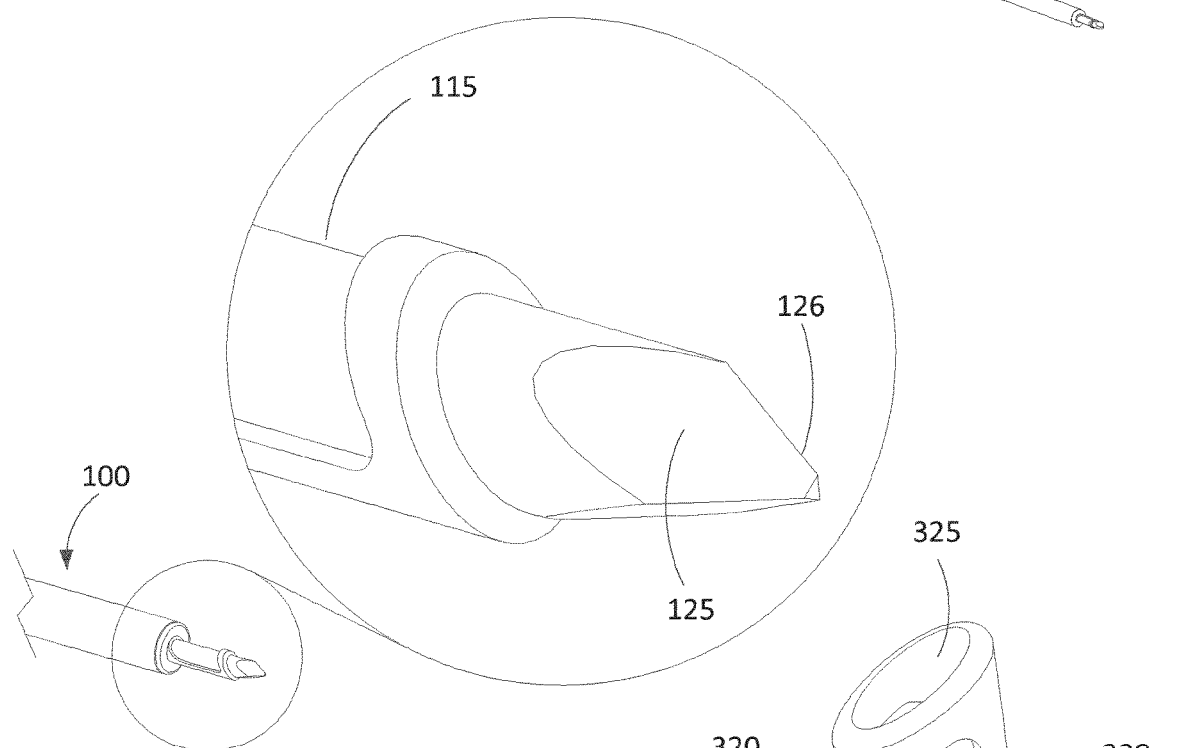
FIG. 2B shows the tack loaded on the stepdown portion of the driver device of FIG. 1.
Figure 2A:
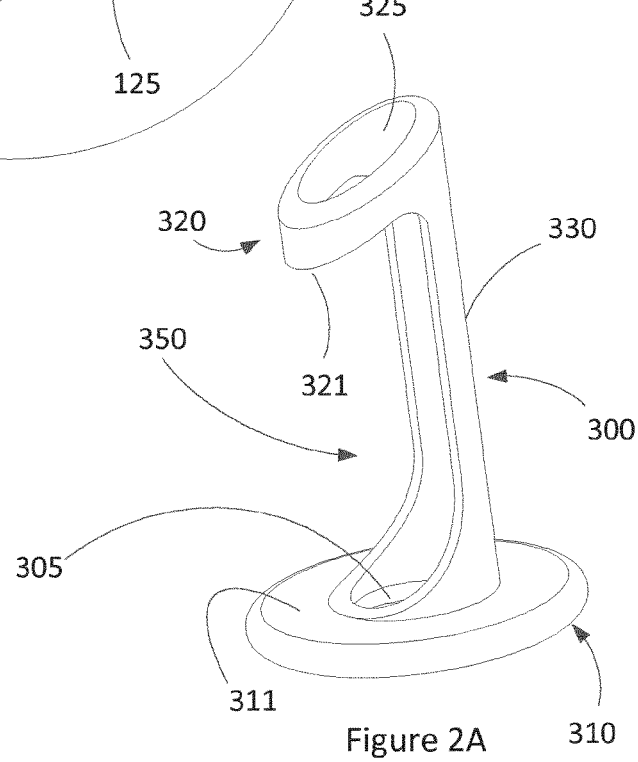
FIG. 2A shows an example of a tack which may be used with a driver device in accordance with the present teaching.
Figure 13:
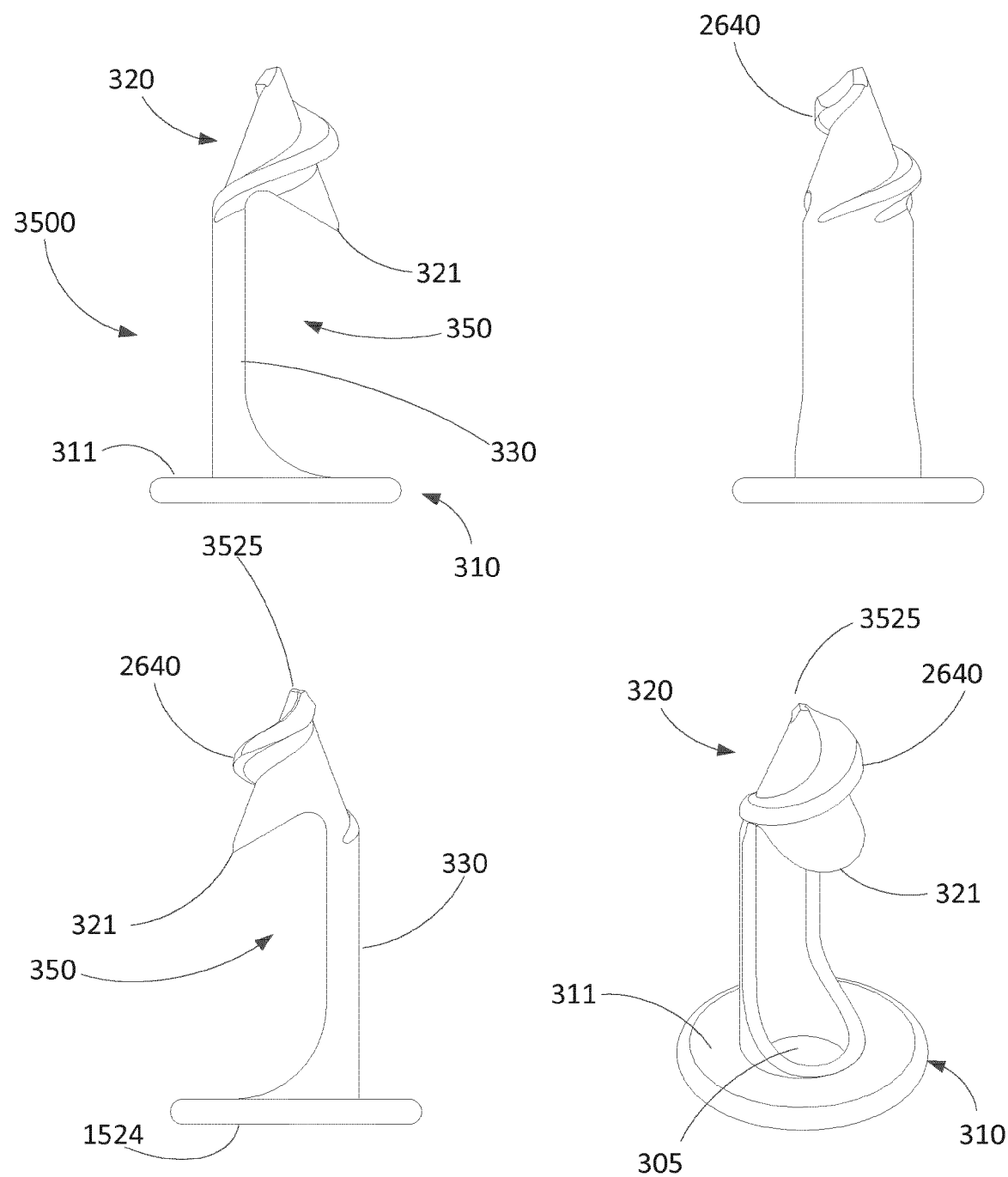
FIGS. 13, 14 and 15 shows plan, elevation and isometric views of alternative embodiments of a tack in accordance with the present teaching.

FIG. 13 shows a further embodiment of the tack of FIG. 2A. The tack of FIG. 13 is different in that the distal tacking portion 320 does not have a distal opening 325 (Refer FIG. 2A). Instead the distal tacking portion is closed such that the tack is ultimately seated on the driver but the driver tip portion does not project through the tack. A thread 2640 is provided on the exterior surface of the distal tacking portion 320, which terminated at a tip 3525 of the tack. A barb 321 is provided such that when the tack receiving portion of the driver device 100 is removed a recessed portion 350 is exposed. This recessed portion 350 is similar to the previously described recess portion in that, on deployment within tissue, the tissue can invaginate into this recess, such that the rearward facing edge 321 now acts as a barb. This thread 2640 is sized such that it does not extend past the barb 321, which is advantageous, in that as the device is rotated, or over rotated, the defect created will not be larger than the barb, which will ensure better retention of the tack within its delivered location.

The tack may be retained on the tip by use of a hydrogel, silicone gel or a haemostatic gel coating on the tip, or the inner lumen surface of the tack, such that stiction provided between the tack and the driver prevents the tack from falling off. Alternately a tack could be configured in such a way that the through bore is arcuate and as such its interaction with the driver would cause a slight interference fit, and prevent it falling off the tip. Alternatively, in an embodiment where a helical or auger style driver tip is provided, the tack could feature an internal threading which interacts with the driver tip, to prevent it falling off. When the tack is deployed and the tip could be retracted by rotation, to disengage the tack.

Figure 16:
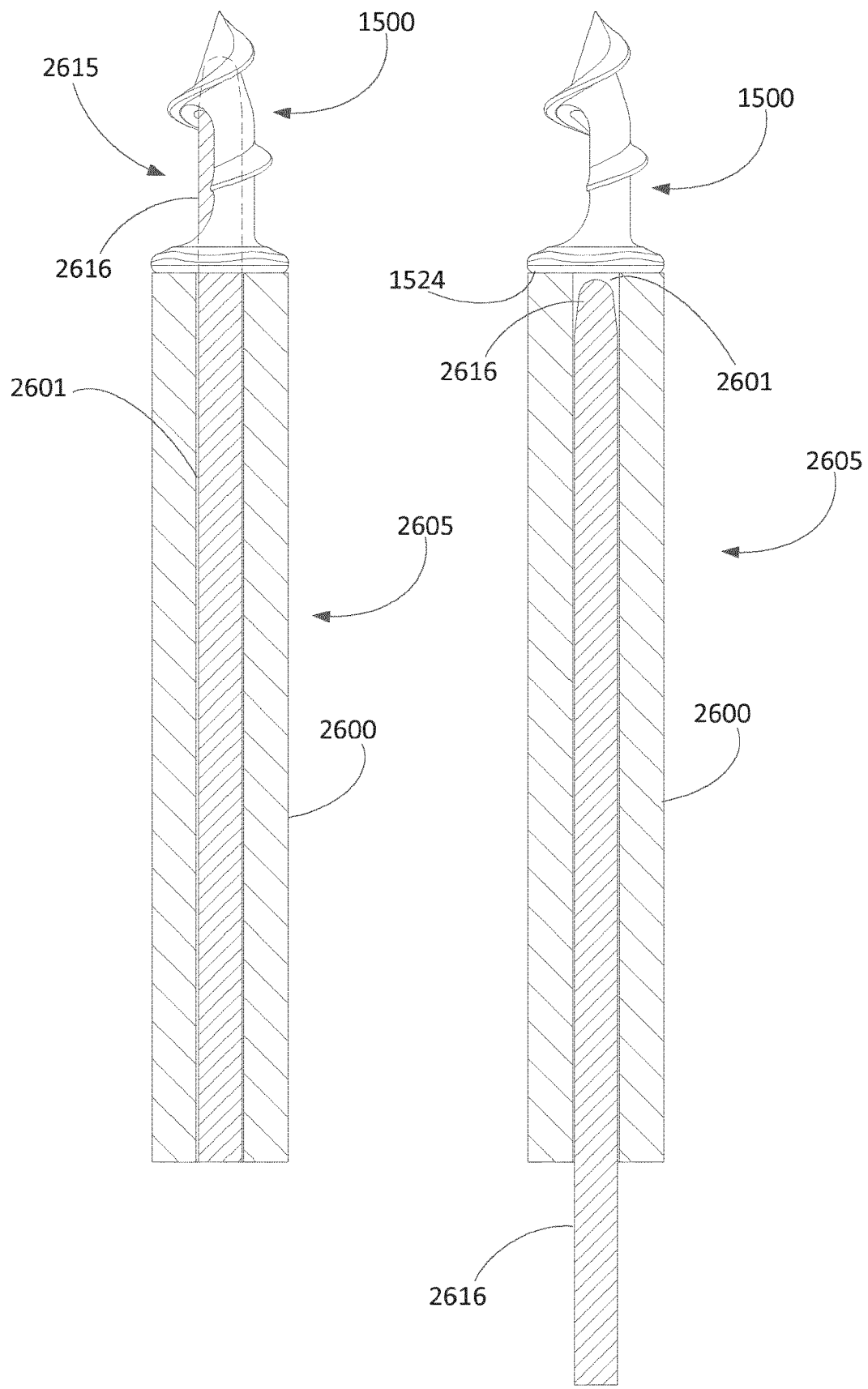
FIG. 16 shows a method of decoupling a tack from a delivery instrument.
Figure 17:
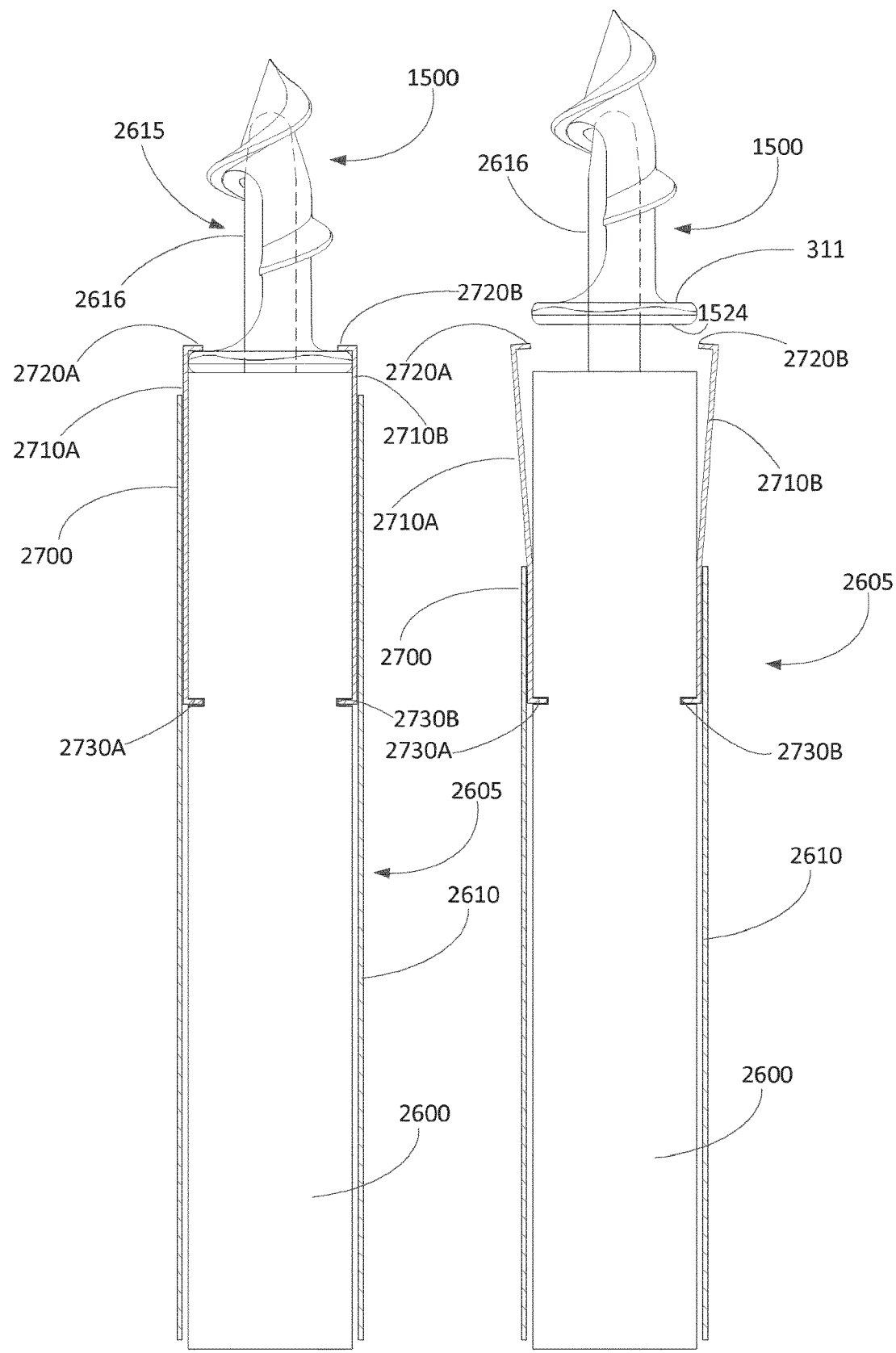
FIG. 17 shows an alternative method of decoupling a tack from a delivery instrument.

In an alternative arrangement to retain the tack on the end of the delivery instrument, such as illustrated in FIGS. 16 and 17, the main shaft 2600 is provided with a lumen 2601. The anchor engaging portion 2616, could be a slight interference fit with the tack 1500. A simple push pull arrangement could be provided to move the anchor engaging portion proximally. When the user is satisfied with the placement of the tack, the needle engaging portion is retracted, which decouples the tack from the delivery instrument. Another embodiment would be to provide the anchor engaging portion 2616 with a clearance fit with the tack 1500. The anchor engaging portion could then be used to push the tack, by being advanced forward. Another variation on this concept (not shown) would be to provide a pusher rod, or rods, which is/are offset from the centre line and engage with the back surface 1524 of the tack.

A further arrangement is illustrated in FIG. 17. Here a pair of outwardly biased clips 2710A and 2710B, retain the tack. An outer tube 2700 retains the clips in the locked position as illustrated in the image on the left of FIG. 17. Each clip has a distal catch 2720, which extends over the surface 311 at the back of the tack. When the shaft 2700 is retracted, as in the image on the right of FIG. 17, the clips spring outwards and free the catches, such that the tack can move off the end of the delivery instrument. A second set of catches 2730 on the proximal end of the clips 2710, interact with a recess in the shaft 2600 to retain the clips on the shaft. In use the distal end of the shaft 2700 is designed to overlap with the catches 2730, thereby maintaining their affixation to the end of the shaft.

An alternative arrangement to the device of FIG. 1 is to present the driver device and tack, but no cartridge. In this arrangement the user would place the tack 300 manually on the stepdown portion 115 of the device. The driver device could then be passed through a trocar, and be used in the inner abdominal space to attach a mesh.

To use the devices of FIG. 2 the user:

a. Places a tack on the stepdown portion of the delivery device;

b. The user then inserts the driver device 100 through a trocar or port to the desired location to place the tack;

c. The user deploys the tack at the desired location by applying pressure and rotating the device;

d. Following successful deployment of the tack, the driver device is retracted out of the body.

e. The user places another tack on the stepdown portion of the delivery device and repeats steps a to d until the user is satisfied with that sufficient affixation has been achieved and f. The device is removed from the trocar or port.

Figure 4A:
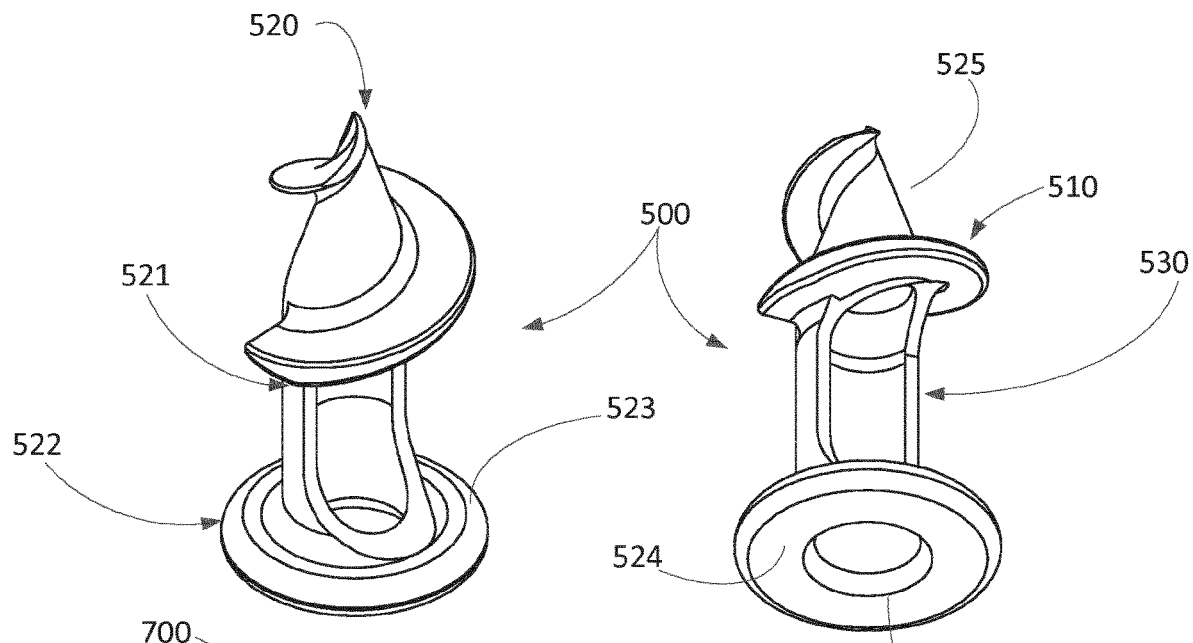
FIG. 4A shows an alternative example of a tack provided in accordance with the present teaching in isometric view.

FIG. 4A shows a further embodiment of a tack 500 that may be usefully employed within the constraint of the present teaching. The tack 500 consists of a distal body section 521. At the distal end of the body section a tip 520 is located. The tip section is shown with a sharp tip geometry, but a non-sharp tip embodiment may also may also employed. Beginning at the tip a helical feature 510 protrudes around the body section. The proximal end of the body section terminates in a tail feature 522. The tail feature 522 is intended to interact with the delivery instrument 600 during delivery. Following delivery through a mesh, the tail element supports the mesh, and retains it in contact with the abdominal wall. The tack also features a lumen 540, such that the tack is hollow. A cut-out section 530 on the main body portion is also provided, which exposes the lumen 540 of the tack. The helical feature 510 facilities the fixation of the tack within the abdominal wall tissue; the area on the underside of the helical protrusion provides a surface upon which abdominal tissue acts to prevent the tack's removal following deployment. In addition to the helix the cut out section 530 provides additional area into which the tissue may invaginate to provide additional anchoring of the tack within the abdominal wall.

Figure 4B:
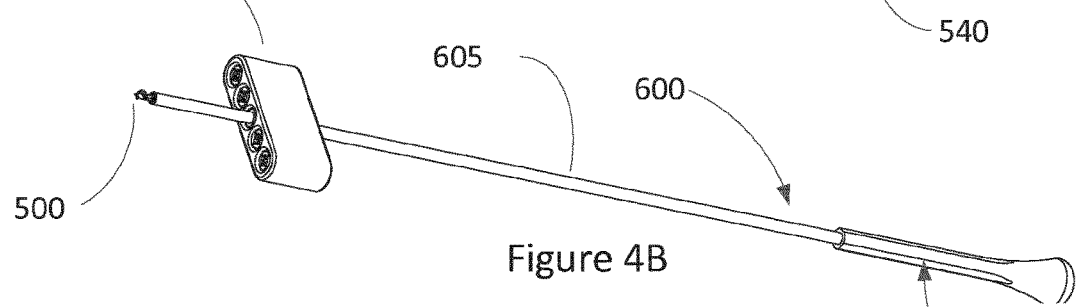
FIG. 4B show an alternative example of a fixation device delivery system or tacking device with cartridge provided in accordance with the present teaching in isometric view.

FIG. 4B shows an example of the delivery system that may be used to deploy such a tack. The delivery instrument 600 consists of a shaft element 605 and a handle feature 610 located at the proximal end. At the distal end a tack 500 is shown loaded on the delivery instrument 600. Deployment of the tack is achieved by inserting the delivery instrument through a trocar (or defect if the surgery is not laparoscopic) in the abdominal wall and positioning the tip of the delivery instrument and the tack at the desired deployment site. Through exertion of longitudinal force as the delivery instrument is rotated tack is deployed. Exertion of force may be achieved manually or through a mechanism. The handle feature 610 provided a means of manual manipulation of the instrument.

Loading the tacks may be achieved in a number of ways, including manually, however FIG. 4B shows a tack cartridge 700 to aid loading. The cartridge is intended to act a storage for the tacks in the device packaging. It also acts as a means of loading tacks onto the delivery instrument. A cartridge capable of storing 5 tacks is shown in FIG. 4B, again the number of actual tacks employed is not limiting.

Figure 10:
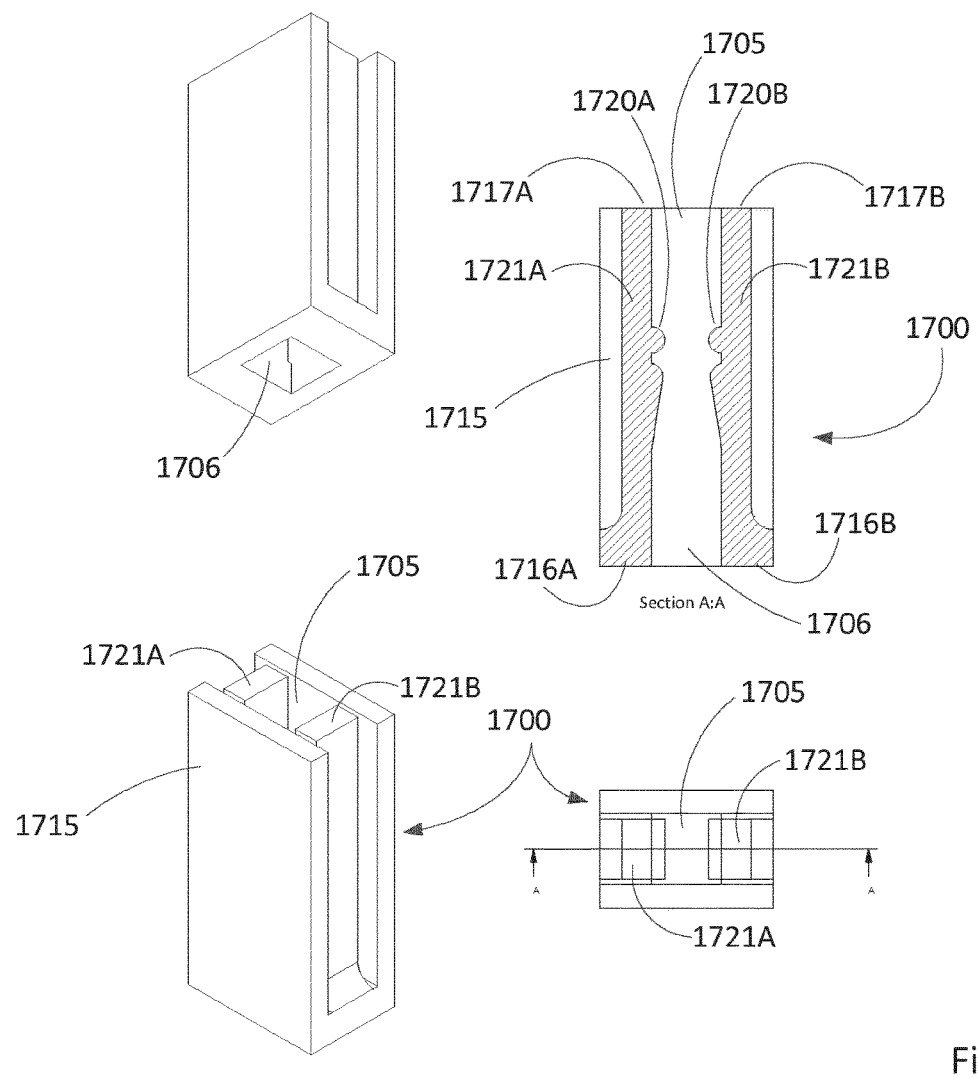
FIG. 10 shows various plan and elevation views in first angle projection, with isometric and sectional views of a portion of a cartridge.
Figure 10:
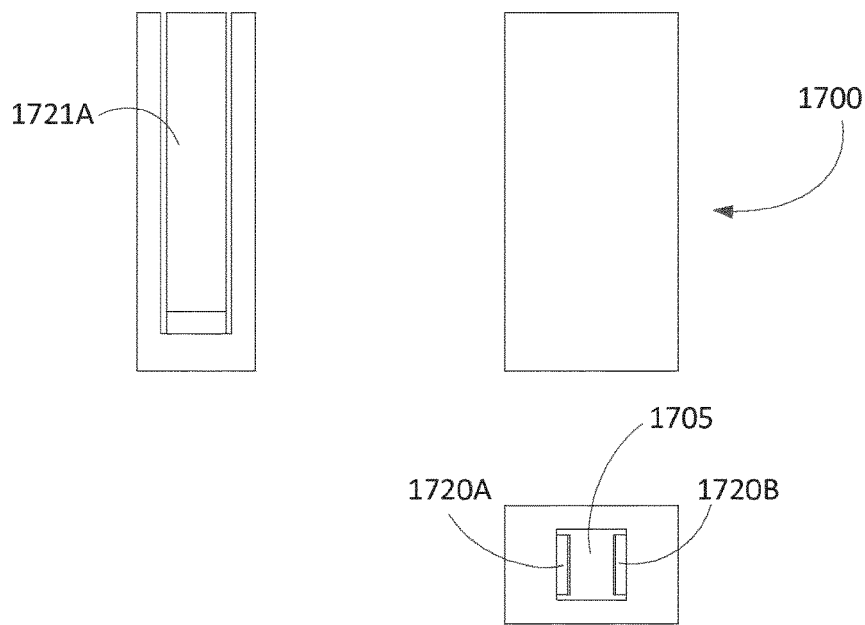

Turning now to FIG. 10, which illustrates a portion of an alternative embodiment of a cartridge. It will be appreciated that the design of this tack in this illustration is different to that of FIG. 4, but the principle of operation of the cartridge is applicable to many of the tack designs outlined in this specification. FIG. 10 illustrates one chamber of the cartridge, it will be appreciated that where there are multiple tacks required this feature could be arranged in number ways. The main purpose of the illustration is to educate on the features necessary to retain the tack with the cartridge and load it onto the delivery instrument.

The cartridge 1700 comprised a main body portion 1715. A pair of fingers 1721A and 1721B are provided. Each finger is attached at its proximal end 1116A and 1716B to the main body portion 1715. The distal end of the finger 1717A and 1717B, illustrated in the section view A-A of FIG. 10, are free to flex from side to side and this resilient nature of the material and geometry of the fingers advantageously retains a tack within the cartridge until a driver engages with the cartridge to effect a displacement of the fingers away from the tack and simultaneously allow for an engagement of the tack with the driver or other delivery instrument.

Figure 11A:
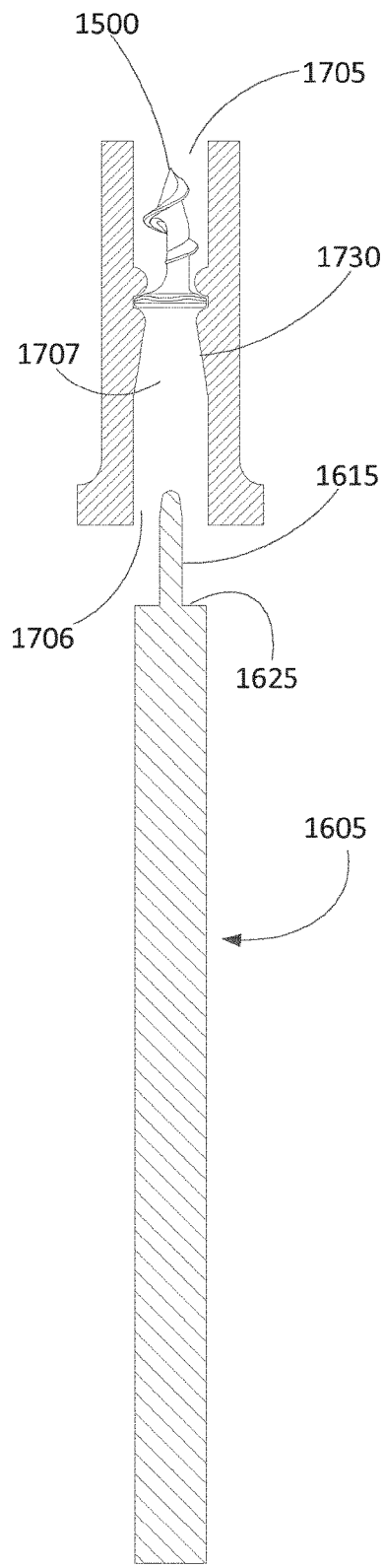
FIGS. 11A to 11C show the device of FIGS. 7 and 8 in use with a cartridge in cross sectional view.
Figure 11B:
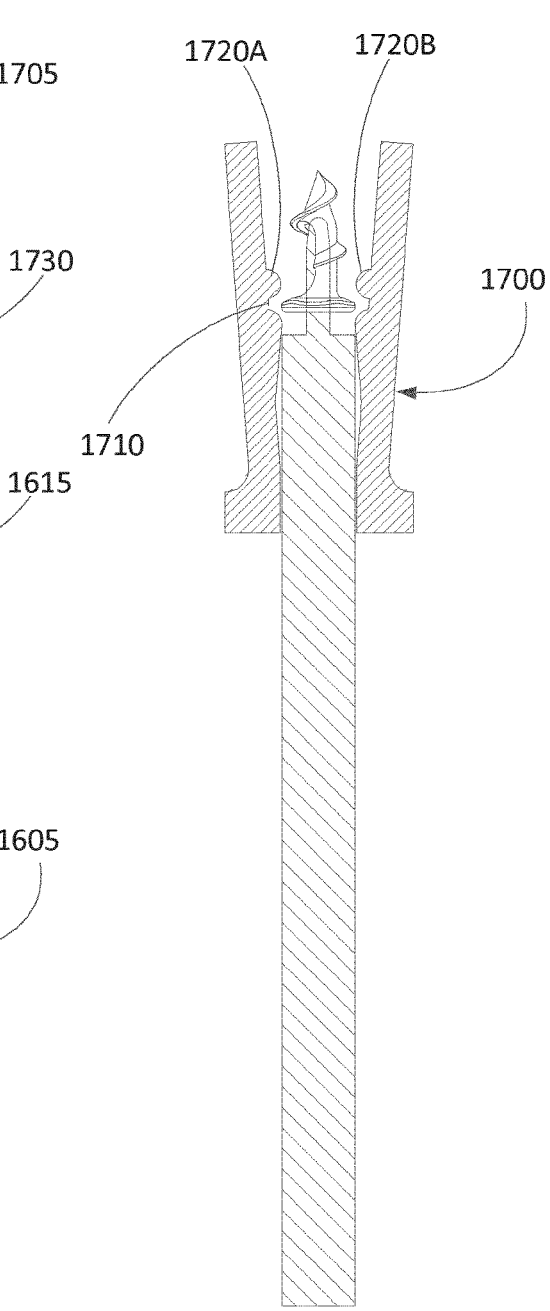
Figure 11C:
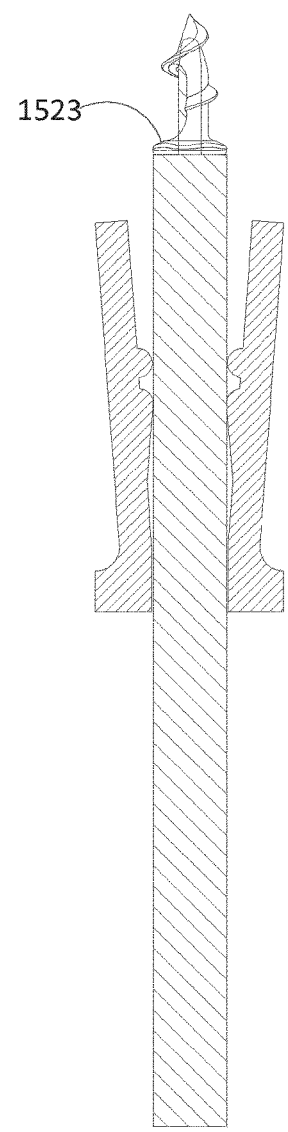

FIG. 11A-11C show the cross section of a portion of a cartridge 1700. The cartridge has a proximal opening 1706 and a distal opening 1705. The delivery instrument tip 1615 enters into the cartridge lumen 1707 though the proximal opening 1706. As the delivery instrument is advanced the shoulder 1625 comes in contact with the tapered surface 1730, which aligns the tip portion of the shaft 1615 with the lumen of the anchor 1540, Ref FIG. 7. The tack 1500 is retained within the recessed feature 1710, and is retained on the distal end by two protrusions 1720A and 1720B. As the delivery instrument is further advanced the protrusions act on the distal surface 1523 of the tack tail feature 1522. This ensures that the tack fully loaded against the shoulder 1625 of the delivery instrument. Further advancement of the delivery instrument causes the tack to be released from the opening 1705.

Referring now to FIG. 4B, here the cartridge 700 is shown towards the distal end of the delivery instrument. Once the tack is loaded this cartridge can be moved towards the handle and remains in that position for the tack placement. The delivery instrument is removed once the tack is delivered and the cartridge is removed and the delivery instrument advanced in to the next lumen containing a tack. The handle, cartridge could be designed to mate, such that the cartridge clicks onto the handle to prevent unwanted longitudinal movement of the cartridge during use.

As the delivery instrument is pushed through the cartridge it engages with a taper 1730 (again referring to FIG. 11), which aligns the delivery instrument tip 1615 with the lumen of the tack. As the delivery instrument is pushed further through the cartridge, the tack is pushed past the protrusions by the force transmitted through the interaction between the shoulder and the tack, allowing the tack to exit the distal opening 1705. The cartridge is retained on the delivery instrument shaft until the tack is deployed and the delivery instrument retracted from the cartridge.

Returning to FIG. 4C and FIG. 4A, which shows the interaction between the delivery instrument and the tack. The delivery instrument has a tip 620 with a diameter that is reduced from that of the shaft 605. This tip section engages with the lumen 540 of the tack. The engagement of the tip with the lumen of the tack ensures that the tip provides stability to the tack during deployment. Additionally, the tip is intended to partially fill the cut out section 530, to ensure a smoother deployment. The reduction in diameter at the tip provides a shoulder 625, on the delivery instrument, through which force can be exerted on the tail feature 522 of the tack. A pushing force along the direction of the delivery instrument can be exerted. Once the tack is deployed and the driver tip disengaged from the tack, the cut out section 530 defines a volume within which tissue may invaginate to further secure the deployed tack within its delivery location.

Figure 4C:
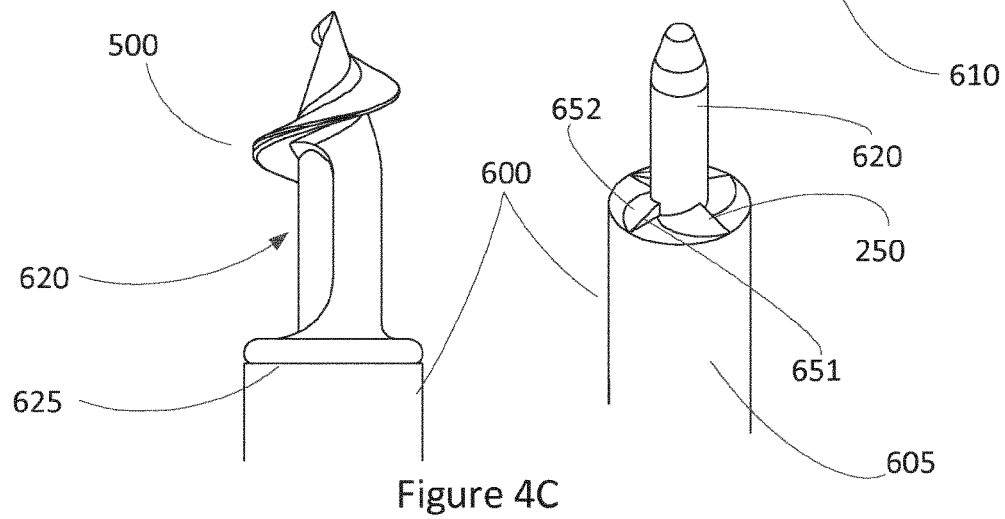
FIG. 4C shows an alternative example of a fixation device delivery system or tacking device provided in accordance with the present teaching in elevation and isometric view.
Figure 5:
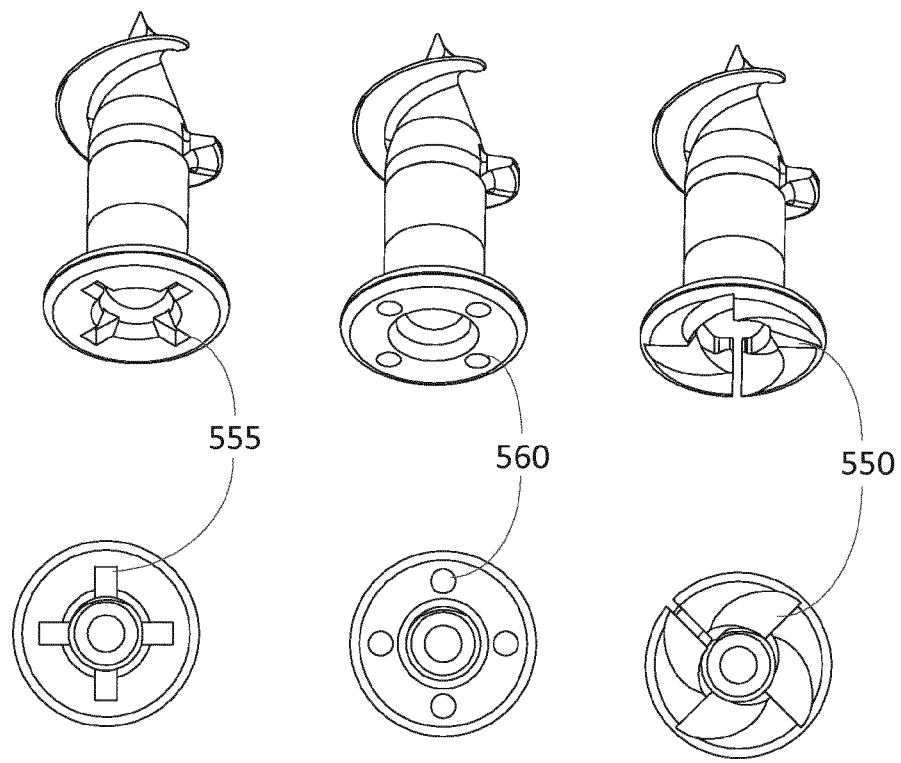
FIG. 5 shows alternative arrangements of tacks that may be usefully employed within the context of the present teaching in isometric and plan view

The tack illustrated in FIG. 4C is a further embodiment of that of FIG. 4A, modified to have recesses on the proximal surface 524 of the tail feature 522. Similar numbering is used for both embodiments. Protrusions 650 from the shoulder 625 allow for rotational forces to be transmitted to the tack. The rotational protrusions 650 are intended to act on similar but opposing features on the proximal surface 524 of the tack tail. An example of such a feature is shown in FIG. 5, where a recess 550 is cut such that it interacts with the protrusions 650. The protrusion 650 comprises a ramp feature 652 and a flat face 251. When the delivery instrument rotated in a clockwise direction the flat face 651 transmits rotational force to the tack. If the delivery instrument is rotated counter clockwise, the tack rides up over the ramp feature and slips before riding over the next ramp and so on. Such a feature may usefully be employed to prevent rotation of the tack in the wrong direction. The advantage of this one way drive is that if the tack is deployed manually, the user may complete multiple full revolutions of the tack, single handed without removal or re-orientation of the delivery instrument within their hand. This would allow the user to maintain a pushing force applied to the tack throughout deployment.

If the tack is excessively rotated the threads may end up macerating tissue in the distal tacking portion. A solution to this would be to provide a torque slip mechanism on the delivery instrument.

FIG. 5 shows further examples of features on the proximal surface of the tack tail. A number of distinct sections 560 are removed from the tail section of the tack, which again reduce the volume of material implanted and can mate with a feature on the shaft. Feature 555 shows a larger single cut out from the tail section. The feature 550 provides an element where rotational forces can be exerted in only one direction.

Figure 6:
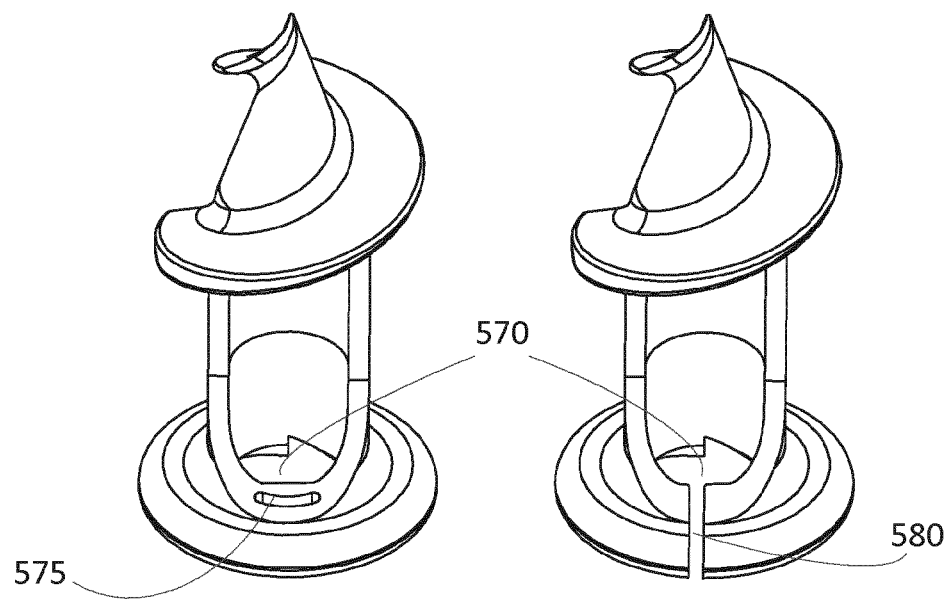
FIG. 6 shows further arrangements of tacks that may be usefully employed within the context of the present teaching in isometric view

FIG. 6 shows methods of retaining the tack on the delivery instrument once loaded. To prevent the tack simply falling of the tip due to gravity a bump feature 570 is provided to interfere with the delivery instrument tip. The interference between 570 and the external diameter of the tip could be accommodated though deformation of the tack or by incorporating features to allow expansion of the tack, such as the slot 580 or the recess 575. These features are not intended to be limiting, as there are many ways of achieving the same effect. For example bump features could be added to the tip portion 620. Alternately, the lumen of the lumen of the tack could be curved slightly to create and interference with the tip portion. Another method would be to coat the proximal surface or interior lumen of the tack with a viscous silicone, such that on interaction with the tip a stiction is created.

FIGS. 7 and 8 show an alternative embodiment of tack device. In previous embodiments the delivery instrument featured a round shaft, whereas in this embodiment, the delivery instrument shaft is square. The tip portion 1615 of the shaft features flats 1620. These flats interact with the square profile lumen 1540 of the tack enabling transmission of torque of the shaft. In some scenarios it may be desirable to rotate the tack in either direction. For example if the surgeon wanted to reposition it after it has been placed through a mesh. In such a scenario the flats shown would be advantageous. While the tack is illustrated with a cartridge, in some cases it may be preferable to manually load the tacks onto the delivery instrument. The shaft illustrated in this embodiment features a ballnose tip 1616, which is advantageous in preventing needlestick injuries.

The design which incorporates a square profile is not intended to be limiting and it will be understood that other profiles could be used to achieve similar benefits.

FIGS. 12A and 12B illustrate an alternative embodiment of the device of FIG. 2B. The tack of both embodiments is similar, however the tip portion 2615 of the delivery instrument 2605 has been modified to include a helical thread 2640. The thread is sized such that it does not interfere with the lumen 540 of the tack. FIG. 12B shows the tack loaded onto the delivery instrument. The advantage of the helical thread on tip portion would be that the tack could be placed in the abdominal wall by rotation, which offers a more controlled method when compared to pushing.

Figure 14:
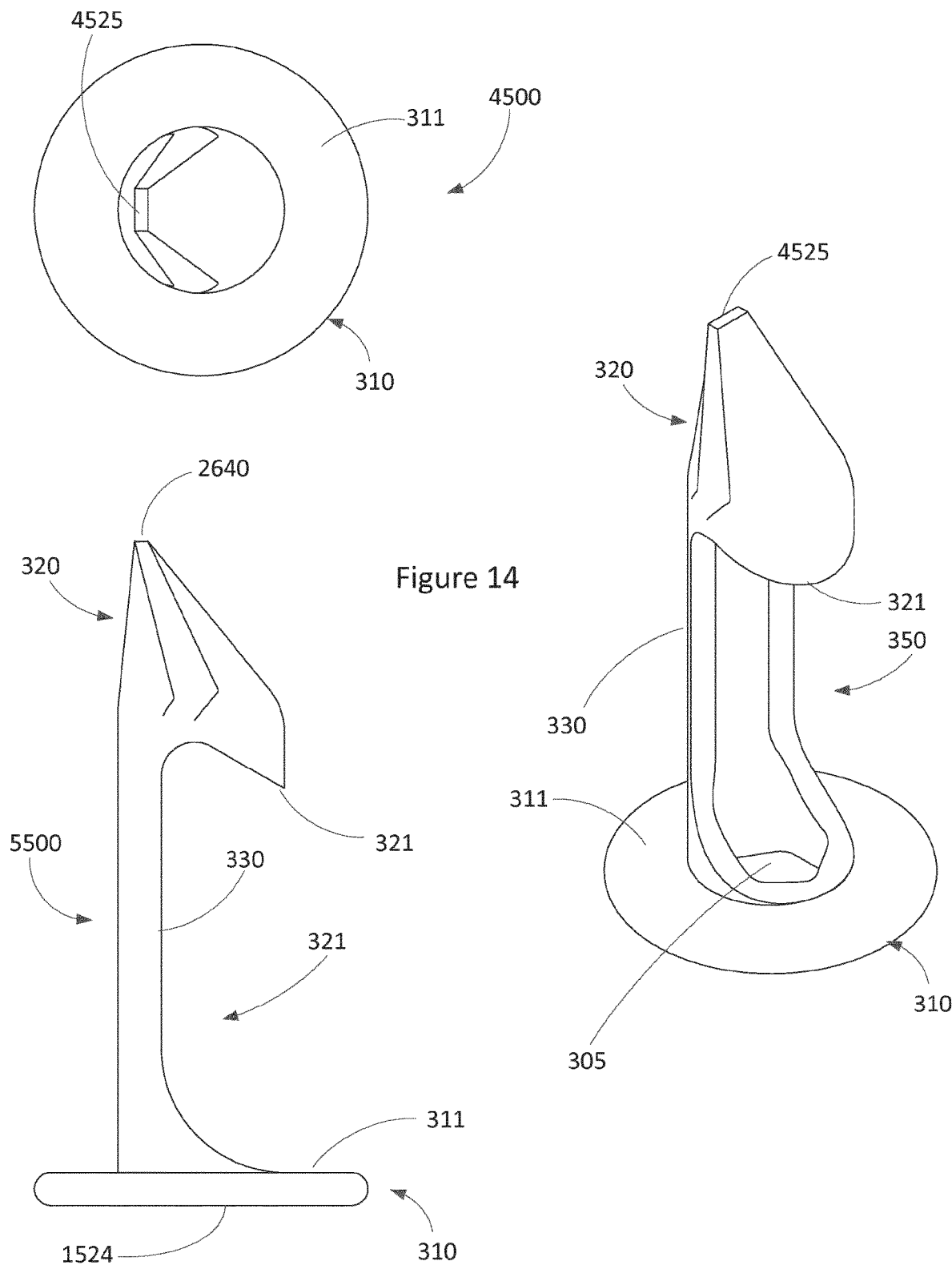
Figure 15:
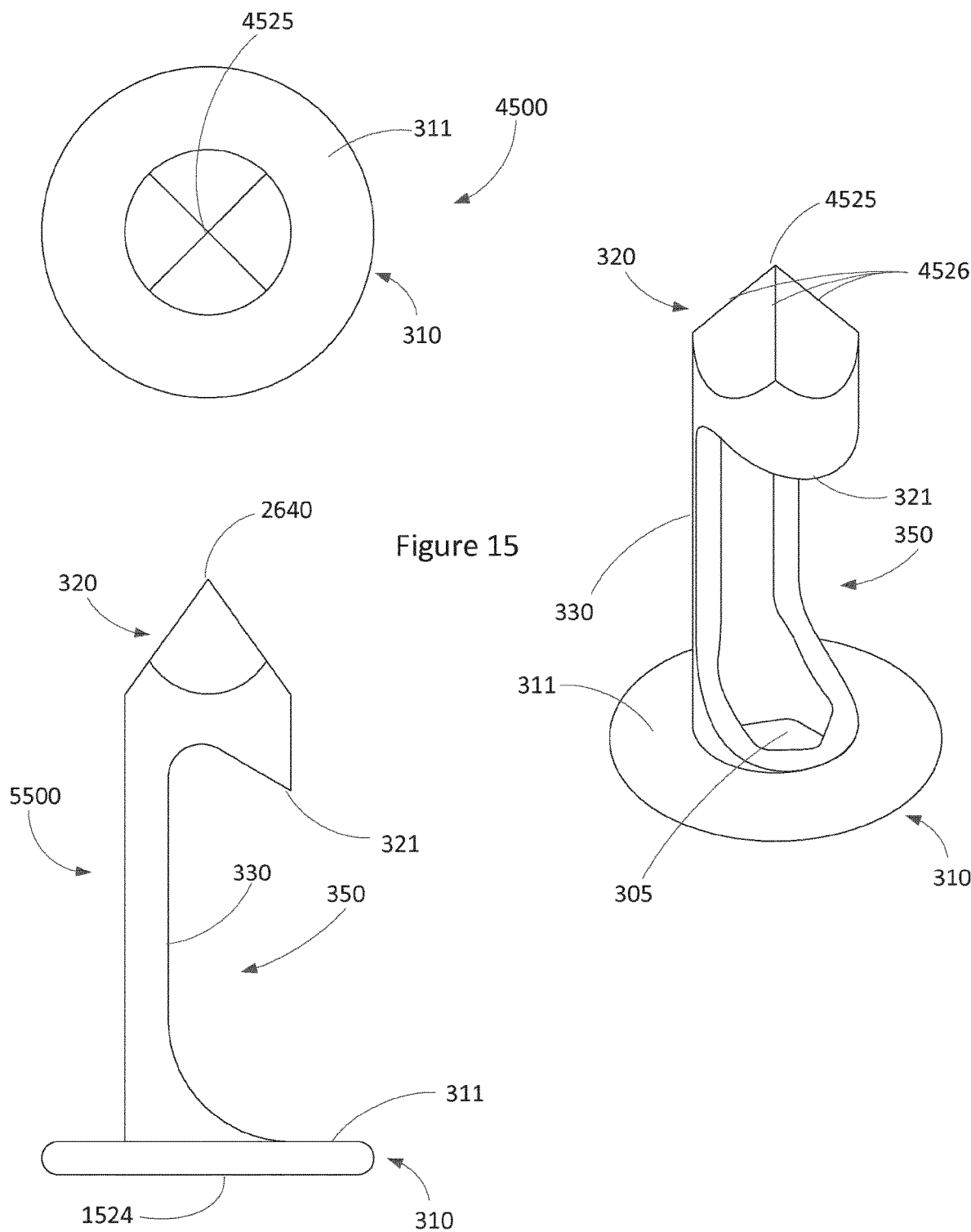

FIGS. 14 and 15 show alternative arrangements of tacks. The tack of FIG. 14 features a hexagonal profile on the lumen 305. The geometry of the distal tacking portion 320 mimics a dissecting trocar. An important feature as illustrated is that the leading edge 4525 is not sharp. The distal tacking portion is slightly longer than some of the tack options presented, but it does have an advantage of the leading edge 4525 being off centre which means the main defect is not in the same plane as the barb 321, making the barb more effective. In the anchor illustrated in FIG. 15, the main difference is that the leading edge 4525 is a sharp tip, and the cutting edges 4526 are provided which may be advantageous over the anchor of FIG. 14 in penetrating meshes with smaller pores.

Use of these devices would not be limited to the inner abdominal space, but could be used in any procedure where a mesh needs affixation, for example and lap inguinal hernia.

It will be appreciated that while preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A tack delivery system for delivery of a tack into tissue within a body, the tack being operably loaded onto a driver device external of the body, the delivery system comprising:
    a driver device comprising a handle coupled to a shaft;
    a tack comprising a body defining a tack lumen; and
    a cartridge in which multiple tacks are operably stored,
    wherein the shaft comprises a distal end featuring a stepdown portion dimensioned to engage with and accommodate at least a portion of the tack lumen thereon, the engagement of the tack and the driver device operably defining a frictional or mechanical bias force between the tack lumen and the driver device that retains the tack on the driver device, and the tack lumen is correspondingly dimensioned to receive at least a portion of the stepdown portion of the driver device, the tack further comprising at least a primary barb having an engagement area that is at least partially occluded on engagement of the tack with the driver device and is operably activated upon removal of the stepdown portion from the tack upon delivery of the tack into the tissue and contact of the tack body with the tissue;
    wherein on contact of the tack body with the tissue a retention force is established, the retention force being greater than the frictional or mechanical bias force between the tack and the driver device, and
    wherein the cartridge comprises a main body portion and a first and second finger which are operably configured to engage with the tack, each finger being attached to the main body portion at a first end and being moveable relative to the main body portion, wherein the fingers are operably biased to retain a tack within the cartridge until the driver device engages with the cartridge to effect a displacement of the fingers away from the tack and simultaneously allow for an engagement of the tack with the driver device or other delivery instrument.

2. The system of claim 1, wherein the tip or other section of the tack lumen is operably offset from the shaft of the driver device to prevent premature deployment of the tack from the driver device.

3. The system of claim 1, wherein the tack comprises a secondary barb or surface configured to assist in deployment of the tack.

4. The system of claim 1, wherein 50% or more of the tack lumen is exposed along a longitudinal axis of the tack body to promote tissue ingrowth after delivery.

5. The system of claim 1, wherein the driver device comprises a non-deformable core wire.

6. The system of claim 1, wherein the driver device comprises a non-deformable core wire rotatable helical tip.

7. The system of claim 1, wherein the handle is an electrically or pneumatically controlled handle configured to rotate and or advance and retract an accommodated tack relative to the shaft.

8. The system of claim 1, wherein the tack comprises a dissecting tip with a triangular profile configured to assist in delivery of the tack.

9. A method of deploying a surgical tack within an abdominal cavity, the method comprising:
   a. providing a delivery system comprising:
      a driver device comprising a handle coupled to a shaft, and
      a tack comprising a body defining a tack lumen, wherein the shaft comprises a distal end featuring a stepdown portion dimensioned to engage with and accommodate at least a portion of the tack lumen thereon, the engagement of the tack and the driver device operably defining a frictional or mechanical bias force between the tack lumen and the driver device that retains the tack on the driver device, and the tack lumen is correspondingly dimensioned to receive at least a portion of the stepdown portion of the driver device, the tack further comprising at least a primary barb having an engagement area that is at least partially occluded on engagement of the tack with the driver device and is operably activated upon removal of the stepdown portion from the tack upon delivery of the tack into the tissue and contact of the tack body with the tissue, and wherein on contact of the tack body with the tissue a retention force is established, the retention force being greater than the frictional or mechanical bias force between the tack and the driver device;
   b. placing a tack on the step-down portion of the driver device;
   c. inserting the shaft of the driver device through a trocar or port to a desired location to place the tack;
   d. deploying the tack at the desired location by applying pressure and rotating the driver device;
   e. placing another tack on the step-down portion of the driver device and repeating steps b to c until the user is satisfied with that sufficient affixation has been achieved; and
   f. removing the driver device from the trocar or port.

10. The method of claim 9 wherein the driver device is reusable.

11. The method of claim 9, wherein the delivery system further comprises a cartridge in which multiple tacks are operably stored.

12. The method of claim 9, wherein the tip or other section of the tack lumen is operably offset from the shaft of the driver device to prevent premature deployment of the tack from the driver device.

13. The method of claim 9, wherein the tack comprises a secondary barb or surface configured to assist in deployment of the tack.

14. The method of claim 9, wherein 50% or more of the tack lumen is exposed along a longitudinal axis of the tack body to promote tissue ingrowth after delivery.

15. The method of claim 9, wherein the driver device comprises a non-deformable core wire.

16. The method of claim 9, wherein the driver device comprises a non-deformable core wire rotatable helical tip.

17. The method of claim 9, wherein the handle is an electrically or pneumatically controlled handle configured to rotate and or advance and retract an accommodated tack relative to the shaft.

18. The method of claim 9, wherein the tack comprises a dissecting tip with a triangular profile configured to assist in delivery of the tack.

19. A method of deploying a surgical tack within an abdominal cavity, the method comprising:
   a. providing a delivery system comprising:
      a driver device comprising a handle coupled to a shaft,
      a tack comprising a body defining a tack lumen, and
      a cartridge in which multiple tacks are operably stored,
      wherein the shaft comprises a distal end featuring a stepdown portion dimensioned to engage with and accommodate at least a portion of the tack lumen thereon, the engagement of the tack and the driver device operably defining a frictional or mechanical bias force between the tack lumen and the driver device that retains the tack on the driver device, the tack lumen is correspondingly dimensioned to receive at least a portion of the stepdown portion of the driver device, the tack further comprising at least a primary barb having an engagement area that is at least partially occluded on engagement of the tack with the driver device and is operably activated upon removal of the stepdown portion from the tack upon delivery of the tack into the tissue and contact of the tack body with the tissue, and wherein on contact of the tack body with the tissue a retention force is established, the retention force being greater than the frictional or mechanical bias force between the tack and the driver device;
   b. inserting the cartridge into a trocar or port;
   c. inserting the shaft of the driver device through the cartridge, picking up a tack in the process of doing so and advancing the distal end of the device to a desired location to place the tack;
   d. deploying the tack at the desired location by applying pressure and rotating the device;
   e. following successful deployment of the tack, retracting the driver device proximal to a main body section of the cartridge so that a next tack can be picked up on the next advancement of the device;
   f. rotating the cartridge to align a next tack; and
   g. repeating steps c to e to deploy the next tack.

20. The method of claim 19, wherein the delivery system further comprises a cartridge in which multiple tacks are operably stored.

21. The method of claim 19, wherein the tip or other section of the tack lumen is operably offset from the shaft of the driver device to prevent premature deployment of the tack from the driver device.

22. The method of claim 19, wherein the tack comprises a secondary barb or surface configured to assist in deployment of the tack.

23. The method of claim 19, wherein 50% or more of the tack lumen is exposed along a longitudinal axis of the tack body to promote tissue ingrowth after delivery.

24. The method of claim 19, wherein the driver device comprises a non-deformable core wire.

25. The method of claim 19 wherein the driver device comprises a non-deformable core wire rotatable helical tip.

26. The method of claim 19, wherein the handle is an electrically or pneumatically controlled handle configured to rotate and or advance and retract an accommodated tack relative to the shaft.

27. The method of claim 19, wherein the tack comprises a dissecting tip with a triangular profile configured to assist in delivery of the tack.

28. A tack delivery system for delivery of a tack into tissue within a body, the tack being operably loaded onto a driver device external of the body, the delivery system comprising:
a driver device comprising a handle coupled to a shaft;
a tack comprising a body defining a tack lumen; and
a cartridge in which multiple tacks are operably stored,
wherein the shaft comprises a distal end featuring a stepdown portion dimensioned to engage with and accommodate at least a portion of the tack lumen thereon, the engagement of the tack and the driver device operably defining a frictional or mechanical bias force between the tack lumen and the delivery device that retains the tack on the delivery force and the tack lumen is correspondingly dimensioned to receive at least a portion of the stepdown portion of the driver device, the tack further comprising at least a primary barb having an engagement area that is at least partially occluded on engagement of the tack with the driver device and is operably activated upon removal of the stepdown portion from the tack upon delivery of the tack into the tissue and contact of the tack body with the tissue,
wherein on contact of the tack body with the tissue a retention force is established, the retention force being greater than the frictional or mechanical bias force between the tack and the driver device, and
wherein the cartridge comprises a tactile feedback element to provide a user with a tactile indication prior to removal of the driver from the cartridge.

29. The system of claim 28, wherein the tip or other section of the tack lumen is operably offset from the shaft of the driver device to prevent premature deployment of the tack from the driver device.

30. The system of claim 28, wherein the tack comprises a secondary barb or surface configured to assist in deployment of the tack.

31. The system of claim 28, wherein 50% or more of the tack lumen is exposed along a longitudinal axis of the tack body to promote tissue ingrowth after delivery.

32. The system of claim 28, wherein the driver device comprises a non-deformable core wire.

33. The system of claim 28, wherein the driver device comprises a non-deformable core wire rotatable helical tip.

34. The system of claim 28, wherein the handle is an electrically or pneumatically controlled handle configured to rotate and or advance and retract an accommodated tack relative to the shaft.

35. The system of claim 28, wherein the tack comprises a dissecting tip with a triangular profile configured to assist in delivery of the tack.

* * * * *